US007608291B2

(12) United States Patent
Baillon et al.

(10) Patent No.: US 7,608,291 B2
(45) Date of Patent: *Oct. 27, 2009

(54) TREATMENT OF INFECTION IN ANIMALS

(75) Inventors: Marie-Louise Baillon, Leicestershire (GB); Catriona Julie Giffard, Leicestershire (GB)

(73) Assignee: Mars, Inc., McLean, VA (US)

( * ) Notice: Subject to any disclaimer, the term of this patent is extended or adjusted under 35 U.S.C. 154(b) by 456 days.

This patent is subject to a terminal disclaimer.

(21) Appl. No.: 10/221,423

(22) PCT Filed: Mar. 9, 2001

(86) PCT No.: PCT/GB01/01036

§ 371 (c)(1),
(2), (4) Date: Feb. 18, 2003

(87) PCT Pub. No.: WO01/65949

PCT Pub. Date: Sep. 13, 2001

(65) Prior Publication Data

US 2003/0195166 A1 Oct. 16, 2003

(30) Foreign Application Priority Data

Mar. 10, 2000 (WO) ..................... PCT/GB00/00890
May 22, 2000 (GB) ................................ 0012401.6
Sep. 11, 2000 (GB) ................................ 0022210.9

(51) Int. Cl.
  *A23K 1/00* (2006.01)
(52) U.S. Cl. ............................. 426/635; 426/2; 424/442
(58) Field of Classification Search ...................... 426/2, 426/635; 424/442; 514/867
See application file for complete search history.

(56) References Cited

U.S. PATENT DOCUMENTS

| 5,219,842 | A * | 6/1993 | Okada et al. .................. 514/54 |
| 6,656,512 | B1 * | 12/2003 | Fone et al. ...................... 426/2 |
| 2003/0143286 | A1 * | 7/2003 | Stevenson et al. ............ 424/602 |
| 2004/0091572 | A1 * | 5/2004 | Bruce et al. ..................... 426/2 |
| 2004/0131659 | A1 * | 7/2004 | Gibson et al. ................ 424/439 |
| 2005/0119222 | A1 * | 6/2005 | Norton et al. ................. 514/54 |
| 2007/0178079 | A1 * | 8/2007 | Zink et al. ............... 424/93.45 |
| 2007/0179197 | A1 * | 8/2007 | Henderson .................. 514/547 |

FOREIGN PATENT DOCUMENTS

| JP | 08173055 | 7/1996 |
| WO | WO 91/18521 | 12/1991 |
| WO | WO 96/39046 | 12/1996 |

OTHER PUBLICATIONS

Roberfroid M. Advances in Experimental Medicine and Biology. Health Benefits of Non-Digestible Oligosaccharides. vol. 427, pp. 211-219, 1997.*

Diez M. et al. Study of Food Fibers in Dogs. Ann Med Vet vol. 142, pp. 185-201, 1998.*

Flickinger E. et al. Glucose Based Oligosaccharides Exhibit Different In vitro Fermentation Patterns . . . American Society for Nutritional Science. vol. 130, pp. 1257-1273, Feb. 1, 2000.*

E. A. Flickinger, et al., "Glucose-Based Oligosaccharides exhibit different in vitro fermentations patterns and affect in vivo apparent nutrient digestibility and microbial populations in dogs," American Society for Nutritional Sciences, Feb. 1, 2000; pp. 167-1273.

G. R. Gibson, et al.; "Aspects of in vitro vivo research approaches directed toward identifying probiotics for human use," American Society for Nutritional Sciences, 2000; pp. 391S-395S.

J. M. Campbell, et al.; "Selected indigestible oligosaccharides affect large bowel mass, cecal and fecal short-chain fatty acids, pH and microflora in rats," American Society for Nutritional Sciences: 1997; pp. 130-136.

D. J. A. Jenkins, et al.; "Inulin, Oligofructose and Intestinal Function," American Society for Nutritional Sciences; 1999; pp. 1431S-1433S.

T. J. Bunce, et al.; "Journal of Animal Science 73, (S85) 70," 1995; 1 page.

T. J. Bunce, et al., "Journal of Animal Science 73 (S1), 69," 1995; 1 page.

G. R. Gibson et al., "Regulatory effects of bifidobacteria on the growth of other colonic bacteria," Jorunal of Applied Bacteriology 1994, 77; pp. 412-420.

X. Wang et al., "Effects of the In vitro fermentation of oligofructose and inulin by bacteria growing in the human large intestine," Journal of Applied Bacteriology 1993, 75; pp. 373-380.

G. A. R. Gebbink, et al., "Effects of addition of fructooligosaccharide (FOS) and sugar beet pulp to weanling Pig diets on performance, microflora and intestinal health," Purdue University, 1999 Swine Day Report, pp. 1-5.

M. B. Roberfrold et al., "The bifidogenic nature of chicory inulin and its hydrolysis products," American Society for Nutritional Sciences, 1997; pp. 11-19.

J. S. Bailey et al., "Effect of Fructooligosaccharide on *Salmonella* colonization of the Chicken Intestine," Poultry Science 70, 1991; pp. 2433-2438.

D. Grizard et al., "Non-digestible oligosachharides used as prebiotic agents: mode of production and beneficial effect on animal and human health," Reprod. Nutr. Dev. 39, 1999; pp. 563-588.

Notice of opposition to a European Patent, dated Aug. 8, 2006; 13 pages.

Epoke J., Coker AO, "Intestinal colonization of rats following experimental infection with Campylobacter jejuni," NCBI, May 1991, 1 page.

(Continued)

*Primary Examiner*—Ralph Gitomer
(74) *Attorney, Agent, or Firm*—Fulbright & Jaworski LLP

(57) ABSTRACT

The present invention relates to the use of a non-digestible carbohydrate in the manufacture of a composition for treating or preventing pathogenic bacteria in the large intestine of a pet animal. It also provides a method for the prevention or treatment of a pathogenic bacteria in the large intestine of a pet animal, the method comprising administering to said pet animal a composition which comprises a non-digestible carbohydrate.

6 Claims, 1 Drawing Sheet

OTHER PUBLICATIONS

Greetham, H.L, et al., "Bacteriology of the Labrador dog gut: a cultural and genotypic approach," Journal of Applied Microbiology, 2002; pp. 640-646.

"Rats" Leicester City Council, environment & planning; web pages obtained on May 22, 2007; 2 pages.

A.H. Sparkes et al. "Bacterial Flora in the duodenum of healthy cats, and effect of dietary supplementation with fructo-iligosaxxharides", AJVR, vol. 59, No. 4, Apr. 1998.

M.D. Willard et al. "Effects of dietary supplementation of fructo-oligosaccharides on small intestinal bacterial overgrowth in dogs", AM J Vet Res, vol. 55, No. 5, May 1994.

A. H. Sparkes et al. "Effect of dietary supplementation with fructo-oligosaccharides on fecal flora of healthy cats", AJVR, vol. 59, No. 4, Apr. 1998.

Z. V. Marshall-Jones "Effects of Lactobacillus acidophilus DSM13241 as a probiotic in healthy adult cats", AJVR, vol. 67, No. 6, Jun. 2008.

J. S. Bailey "Control of Salmonella and Campylobacter in poultry production. A summary of work at Russell Research Center", Poultry Science 72, pp. 1169-1173, 1993.

L. K. Dick et al. "Microplate subtractive hybridization to enrich for bacteroidales genetic markers for fecal source identification" Applied and Environmental Microbiology, Jun. 2005, pp. 3179-3183.

\* cited by examiner

TREATMENT OF INFECTION IN ANIMALS

BACKGROUND OF THE INVENTION

This application is the U.S. National Stage of International Application No. PCT/GB01/01036, which was filed on Mar. 9, 2001. This application further claims foreign priority to PCT/GB00/00890 filed on Mar. 10, 2000, United Kingdom Application 0012401.6 filed on May 22, 2000, and United Kingdom Application 0022210.9 filed on Sep. 11, 2000.

1. Field of Invention

The present invention relates to the use of a non-digestible carbohydrate in the manufacture of a composition for treating or preventing pathogenic bacteria in the large intestine of a pet animal. It also provides a method for the prevention or treatment of a pathogenic bacteria in the large intestine of a pet animal, the method comprising administering to said pet animal a composition which comprises a non-digestible carbohydrate.

2. Related Arts

Presence of pathogenic bacteria (including infection) of the large intestine in a pet animal is concerning. Particular pathogenic bacteria which infect the large intestine include Campylobacter and pathogenic *Escherichia coli*. The bacterial species responsible for the majority of human bacterial gastrointestinal infections is *Campylobacter jejuni*. This species is also the main cause of concern for cats and dogs. The species can act as a pathogen in young dogs and cats and is likely to be opportunistic in older animals. Clinical illness in dogs manifests itself as diarrhoea ranging from mild to mucus laden bloody diarrhoea, tenesmus, vomiting, anorexia and depression.

A major concern regarding Campylobacter infection in pet animals is the zoonotic risk which carriage and excretion of the organism represents. It has been estimated that 5% of all human *Campylobacter jejuni* induced diarrhoea results from exposure to infected cats or dogs. A number of more recent studies quote dog ownership as a significant risk factor for becoming ill with Campylobacter. A study carried out in Christchurch, New Zealand found that household contact with dogs carried a risk of 1.25 to 2 times normal for contracting Campylobacter.

*E. coli* is a Gram negative facultative anaerobic bacillus. In general it leads a synbiotic life with its host causing it no harm. However specific groups are known to cause gastrointestinal disease and are classified into categories as defined by their virulence mechanisms. Enteropathogenic and verocytotoxigenic strains of *E. coli* are particularly important in causing acute and chronic diarrhoea in dogs. The verocytotoxigenic *E. coli* are thought to be important in diarrhoeic as well as healthy cats and these animals are likely to act as a reservoir of infection for humans.

Salmonella organisms are Gram negative, facultative anaerobic bacteria that are able to survive intracellularly. Salmonella can cause clinical and subclinical infections in dogs and cats as well as humans. This makes them a key organism of interest.

Various studies have found Salmonella to be carried by between 1 and 30% of healthy domestic pet dogs and between 1 and 18% of healthy domestic pet cats. This data is dependent on the survey and whether Salmonella could be cultured from the faeces of animals both with and without diarrhoea.

Clinical infections of Salmonella in animals often display signs of mild to severe gastroenteritis. In dogs, symptoms most often reported are diarrhoea, vomiting, fever, malaise, anorexia, vaginal discharge and sometimes abortion. In cats, diarrhoea, vomiting, fever, malaise and anorexia are the predominant symptoms reported. Recovery from acute Salmonellosis typically occurs within 1 week but can take up to 3 to 4 weeks. Shedding of Salmonella in faeces can continue for 3 to 6 weeks and can be a source of infection for human family members.

Due to the long term shedding of Salmonella, animals are important vectors for non-foodborne infections in humans. Dogs have a greater zoonotic potential than cats although cats have been shown to shed organisms orally, conjunctivally and faecally. Contact with faeces from infected pets is an important source of infection to young children.

The location of Salmonella infection is in the small intestine but due to the potential zoonotic risk from long term shedding of Salmonella in faeces from dogs, a model of the large intestine has been used for this investigation. If viable Salmonella numbers can be reduced while in the large intestine then the duration of shedding can be reduced. Reducing the time that Salmonella is shed in dog faeces also reduces the chance of human contact with the pathogen.

Accordingly, there is a need for a means of preventing or treating pathogenic bacteria in the large intestine of pet animals to eliminate the aforementioned risks. Current treatments for Campylobacter and pathogenic *E. coli* infections and the presence of Salmonella involve administering antibiotics to the pet animals. There are concerns that the continued use of antibiotics in treating Campylobacter infections may lead to the emergence of antibiotic resistant strains of this organism and may have an effect on the long-term health of pet animals (which would reduce or eliminate treatment options). A need therefore exists to find an alternative to antibiotic treatment for infected or infectable animals. The present invention provides such a means.

BRIEF SUMMARY OF THE INVENTION

According to the present invention there is provided the use of a non-digestible carbohydrate in the manufacture of a composition for the prevention or treatment of pathogenic bacteria in the large intestine of a pet animal.

In general, non-digestible carbohydrates comprise those compounds which are not digested by mammals but may be metabolised by intestinal bacterial species belonging to the normal microflora for example, bifidobacteria and lactobacilli.

The term "non-digestible carbohydrate" includes oligosaccharides such as fructooligosaccharide (FOS), galactooligosaccharide (GOS), lactosucrose, maltooligosaccharide, xylooligosaccharide, inulin, fractionated inulin, and raffinose, as well as a dietary fibre component such as coconut endosperm fibre, beet pulp (such as sugar beet pulp), chicory (including chicory pulp), rice bran, carob bean or gum talha.

Oligosaccharides are naturally occurring compounds which can be found in a variety of fruits and vegetables such as bananas, tomatoes, artichokes, onions, garlic and cereals (eg wheat and barley). There are three varieties of FOS:1-kestose, nystose, and B-fructofuranosylnystose. While FOS can be extracted from plants such as those mentioned above, they can also be formed artificially by adding one, two or three fructose units to a sucrose molecule by a B-(2-1)-glycosidic linkage of the fructose unit(s) to the fructose unit of sucrose. Similar artificial linking can be used to synthesize GOS and other oligosaccharides. FOS and GOS are synthetically made and sold. A single or multiple oligosaccharide may be used. One or more may be from a natural source or may be synthetic.

A single or multiple dietary fibre component may be used. The dietary fibre component may comprise or be derived from one or more of: coconut endosperm fibre, beet pulp, chicory, citrus pulp, rice bran, carob bean or gum talha. A single or multiple dietary fibre component may be used in combination with a single or multiple oligosaccharide.

Fresh coconut endosperm is an example of a dietary fibre component of the present invention. It has a typical nutrient distribution of water (35%), oil (44%), protein (6%), sugars (7%), fibre (3%) and ash (1%). However, the form of the coconut endosperm fibre for use according to all aspects of the present invention is not limiting. The coconut endosperm fibre may be fresh or in any other form such as copra, defatted copra (also referred to, amongst others, as copra cake, copra presscake or copra meal) coconut flour, defatted coconut flour, full or defatted desiccated coconut, copra, or degraded coconut endosperm which has been heated or enzymatically treated.

Copra is a particularly suitable source of coconut endosperm fibre for use according to the present invention. Copra is dried coconut endosperm (usually sundried). Defatted copra is also particularly suitable. Defatted copra is the typical result of coconut endosperm which has been dried and had the coconut oil mechanically removed. Defatted copra cake is obtained by first obtaining copra, then crushing the copra through a press or expeller to remove most of the oil. The residue remaining is termed copra cake, copra presscake, or copra meal.

One of the products of complex carbohydrate fermentation in the large intestine by normal microflora are short chain fatty acids (SCFAs). The production of SCFAs by the gut microflora results in a decrease in the pH of the lumen of the large intestine/colon. However, not all intestinal bacteria can metabolise non-digestible carbohydrates. Studies show that pathogenic bacteria are unable to process non-digestible carbohydrates. For this reason these non-digestible carbohydrates in the gut are involved in selectively stimulating the growth of the gut microflora creating a healthier gastrointestinal environment.

The non-digestible carbohydrate of the invention may be one which (additionally) selectively stimulates the growth and/or activity of one or a limited number of beneficial bacteria in the large intestine of a pet animal. The term "beneficial bacteria" refers to those species of bacteria which have a beneficial effect on the host organism. The beneficial species of bacteria typically comprise one of more of bifidobacteria and lactobacilli.

A non-digestible carbohydrate of the present invention may be a "prebiotic". A prebiotic is defined in the art as a non-digestible food ingredient that beneficially affects the host by selectively stimulating the growth and/or activity of one or a limited number of bacteria in the colon, that have the potential to improve health.

Embodiments of the present invention have been shown to have potential in lowering the pH of the large intestine. Using an oligosaccharide, a lowering of the pH in the large intestine model from 7.25 to 5.5 was observed. In the large intestine, a lowering of the pH affects the survival of pathogenic bacteria. In the present invention, a lowering of pH from 7.25 to 5.5 as a result of the inclusion of FOS and/or GOS, is sufficient to eliminate viable *Campylobacter jejuni* bacteria. In contrast, the inclusion of coconut endosperm fibre in the large intestine results in the elimination of viable *Campylobacter jejuni* bacteria without a significant change in the pH of the large intestine (the pH was lowered from 7.0 to 6.5 in the large intestine model).

The present invention provides feeding pet animals with a composition comprising a non-digestible carbohydrate to reduce or eliminate viable pathogenic bacteria in the large intestine.

The pathogenic bacteria of the present invention typically include one of more of Campylobacter, pathogenic Clostridium, Salmonella and pathogenic *Escherichia coli*, such as verocytotoxigenic *E. coli*, for example *E. coli* O157. Of particular interest for the present invention are the species *Campylobacter jejuni* and *Salmonella enterica* (including *S. enterica* serotype Typhimurium). *Campylobacter jejuni* may cause clinical illnesses including diarrhoea, tenesmus, vomiting, anorexia, depression, inflammatory intestinal disease and other intestinal disorders.

The pet animal of the present invention is preferably a mammal, most preferably a mammal having a single stomach as seen in a dog or a cat. The pet animal is preferably not a ruminant and not a production animal (suitable for meat production). The pet animal is preferably a cat or a dog. Cats and dogs according to the present invention are preferably *Felis domesticus* or *Canis domesticus*.

The composition for the prevention or treatment of a pathogenic bacteria in the large intestine of a pet animal is preferably a pet food product The form or type of the pet food product is not limiting. It may be packaged. In this way, the consumer is able to identify, from the packaging, the ingredients in the food product and confirm that it is suitable for the particular pet animal in question. The packaging may be metal (usually in the form of a tin or flexifoil), plastic, paper or card. The pet food product may be a dry, semi-moist or a moist (wet) product. Wet food includes food which is sold in tins and has a moisture content of 70 to 90%. Dry food includes food having a similar composition, but with 5 to 15% moisture and presented as small biscuit-like kibbles. Semi-moist products have a moisture content between wet and dry products. The moisture content is in the range of from 15 to 70%. The amount of moisture in any product may influence the type of packaging which can be used or is required.

In combination with the non-digestible carbohydrate, the remaining components of the pet food product are not essential to the invention and typical standard products can be combined with the required non-digestible carbohydrate. Most preferably, the combined ingredients of the pet food product according to the invention provide all of the recommended vitamins and minerals for the particular pet in question, (a complete and balanced food), for example, as described in National Research Council, 1985, Nutritional Requirements for Dogs, National Academy Press, Washington D.C. (ISBN: 0-309-03496-5); National Research Council, 1986, Nutritional Requirements of Cats, National Academy Press, Washington D.C. (ISBN: 0-309-03682-8) or Association of American Feed Control Officials, Official Publication 1996.

The pet food product according to the present invention encompasses any product which a pet consumes in its diet. Thus, the invention covers standard food products as well as pet food snacks (for example, snack bars, pet chew, crunchy treat, cereal bars, snacks, biscuits and sweet products). The food product is preferably a cooked product. It may be in the form of a gelatinized starch matrix. It may be in the form of chunks in gravy, jelly, loaf or water. It may incorporate meat or animal derived material (such as beef, chicken, turkey, lamb, pork, fish, blood plasma, marrow bone etc or one or more thereof). The product alternatively may be meat free (preferably including a meat substitute such as soya, maize gluten or a soya product) in order to provide a protein source. The product may contain additional protein sources such as soya protein concentrate, milk proteins, gluten etc. The product may also contain a starch source such as one or more grains (e.g. wheat, corn, rice, oats, barley etc), or may be starch free. A typical dry dog or cat food contains about 20-30% crude protein and about 10-20% fat, the remainder being carbohydrate, including dietary fibre and ash. A typical wet, semi-wet or moist product contains (on a dry matter basis) about 40% fat (from 20 to 50%), 50% protein (from 40 to 60%) and the remainder being fibre and ash.

The pet food product is preferably a commercial pet food product. Such a product is preferably sold as a product for feeding to a pet animal, in particular a pet cat or a pet dog.

The pet food product may comprise from 0.1 to 5 weight % of an oligosaccharide, most preferably from 0.1 to 2 weight % (on a dry matter basis).

The level of non-digestible fibre incorporated into a pet food product such as a dietary fibre component is not limiting. Preferably, the fibre component is present in the pet food product at a level of from approximately 0.15 to 8% on a dry matter basis, preferably 0.15 to 5% on a dry matter basis as measured by the Englyst method (as defined in Englyst H. N., and Cumming J. H. (1984), simplified method for the measurement of total non-starch polysaccharides by gas-liquid chromatography of constituent sugars as alditol acetates. *Analyst*. 109, 937-942, and incorporated herein by reference). The levels, as calculated by this method, may go from 0.15% up to 5%, 6%, 7% or 8%. The lower limit may be from 1.5%, 2% or 3%. A description of the Englyst method is described in Appendix 1. In principle, starch is removed enzymatically after solubilisation and NSP is measured as the sum of the constituent sugars released by acid hydrolysis. The starch component of the fibre source is gelatinised by boiling in hot water and is then removed with alph-amylase and pullulanase. Starch and modified, or resistant starch are dispersed in DMSO. Three samples are then subjected to complementary procedures measuring (I) total NSP (ii) water-soluble NSP and (iii) cellulose. Components are hydrolysed in each case with sulphuric acid. The constituent sugars are converted to alditols and are measured as their alditol acetates using gas-liquid chromatography (GLC). Values for total dietary fibre as well as insoluble and soluble fractions can be obtained. Cellulose can be measured separately and the non-cellulose polysaccharides are characterised by measurement of the individual monosaccharides.

The incorporation of the level of coconut endosperm fibre as an example of dietary fibre according to the invention (which may differ according to the form of the coconut endosperm, for example copra or desiccated coconut) can easily be determined by identifying the amount of dietary fibre in the particular form of the coconut endosperm fibre. For example, according to the Englyst method (Supra) defatted copra contains approximately 33.5% total dietary fibre. Accordingly, the preferred amount of defatted copra in a pet food product in order to provide a preferred fibre level of from approximately 0.15 to 5% on a dry matter basis according to the first aspect of the invention is at a level from approximately 0.5 to 15% on a dry matter basis of the pet food product.

Without limiting the present invention, the addition of a non-digestible carbohydrate into a pet food product is believed to maintain good health of the large intestine or improve it, generally achieved by optimising the conditions for growth and multiplication of non-harmful bacteria in the large intestine and/or by lowering the pH of the lumen of the large intestine thereby reducing the amount of harmful bacteria in the large intestine.

A second aspect of the invention provides a method for the prevention or treatment of pathogenic bacteria in the large intestine of a pet animal, the method comprising administering to said pet animal a composition which comprises a non-digestible carbohydrate. The administration is preferably feeding, most preferably feeding by mouth.

Preferred features for the second aspect of the invention apply as for the first aspect mutatis mutandis, such as preferred non-digestible carbohydrates, preferred levels in a pet food product, preferred animals and relevant pathogenic bacteria.

In the second aspect of the invention, the method is preferably administered to a pet animal in need of the prevention or treatment of a pathogenic bacteria in its large intestine. This may be to, for example a young pet animal, such as a puppy, or an older pet animal. Where the composition is a pet food product, the pet food product may be administered in a dietary regime in accordance with the usual dietary regime of the pet animal. The pet food product may comprise 100% of the diet of the pet animal or a lesser proportion, depending on the level of prevention or treatment required. The pet food product allows the non-digestible carbohydrate to be administered with ease thus avoiding a need to supplement the pet animal's food. In addition the pet food product can be administered by the animal's owner thus avoiding constant veterinary supervision. The pet food product may be available at any outlet selling pet food products or may be available from a veterinarian. The pet food product may be as described above according to the first aspect of the invention.

As used herein, the term "administration" also includes feeding or any other method of oral administration. Other means of administration may include tablets, capsules, injection, suppositories or any other suitable means.

A third aspect of the present invention provides a process for the manufacture of a pet food product as defined herein comprising mixing together ingredients with the non-digestible carbohydrate and optionally forming a pet food product. Heating/cooking may be applied to any one or more of the ingredients or non-digestible carbohydrate prior to, during or following the mixing.

Preferred features for the third aspect of the invention apply as for the first or second aspect mutatis mutandis.

DETAILED DESCRIPTION OF THE DRAWINGS

The invention will now be described with reference to the following non-limiting figures, in which.

DETAILED DESCRIPTION OF THE INVENTION

Figure 1:
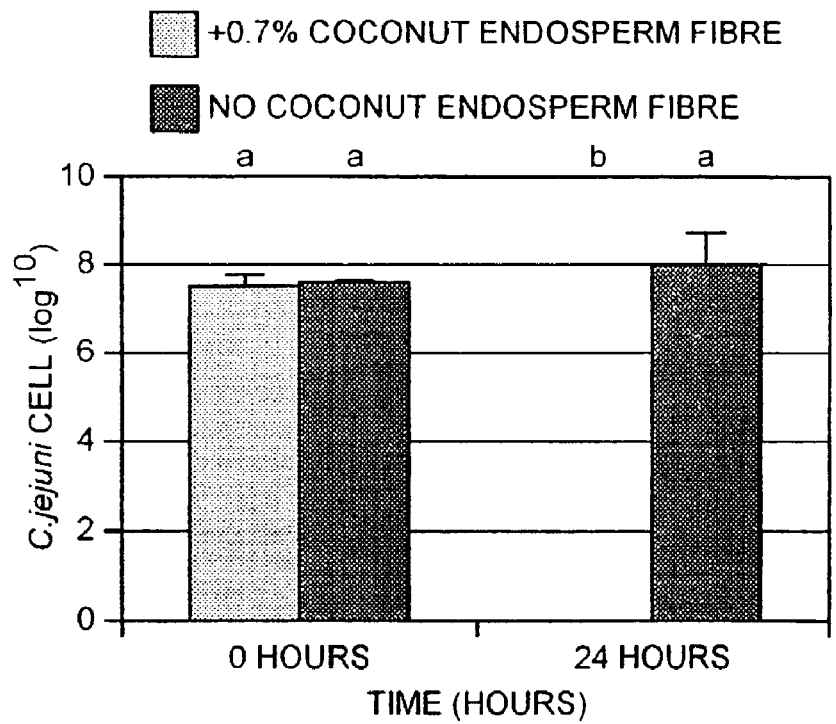
FIG. 1 is a graph of *C. jejuni* cells at 0 and at 24 hours in incubation with or without coconut endosperm fibre.

The invention will now be described with reference to the following, non-limiting examples:

EXAMPLE 1

The Effect of Fructooligosaccharide (FOS) on the Survival of *Campylobacter jejuni* in a Model of the Canine Intestine Method

*Campylobacter jejuni* cells were grown from stock cultures and cultured at 37° C. under microaerobic conditions (5% O$_2$, 10% CO$_2$ and 85% N$_2$). Liquid cultures were grown in 20 ml volumes in 50 ml conical flasks shaken on an orbital shaker. Overnight cultures grown in Mueller Hinton (MH) broth (Oxoid) were adjusted to A$_{600}$ 1.0 before inclusion in the assay.

Flasks were set up with 200 ml MH broth, 1 ml of the adjusted *Campylobacter jejuni* culture, and 2 g fresh faeces. To test flasks, 1.4 g FOS (CoSucra) was added and swirled to mix. Control flasks had no further additions.

Flasks were sampled at the start (0 hours) and end (24 hours) of the experiment to determine viable counts of *Campylobacter jejuni* cells by serially diluting samples from the flasks and plating dilutions onto Campylobacter selective agar (LabM). Plates were incubated microaerobically for 48 hours and which, viable numbers were determined.

At the end of the experiment the pH of the mixture in each flask was determined using Multistix (Bayer).

The experiment was conducted six times using a faecal sample from a different dog each time. All dogs were fed a complete and balanced dry pet food formula for the duration of the study.

Results

After a 24 hour microaerobic incubation, no viable *Campylobacter jejuni* cells could be recovered from flasks that had FOS added. In contrast, *Campylobacter jejuni* cells were recovered from the flasks that contained no FOS at around 10$^7$ cells per ml. The results from the 6 individual experiments are shown in Table 1.

TABLE 1

Numbers of viable *Campylobacter jejuni* cells (log$_{10}$) recovered from the model of the canine large intestine with and without the addition of FOS.
←----log$_{10}$ colony forming units of *Campylobacter jejuni* ---→

| Faecal Sample | 0 hours +0.7% FOS | 0 hours NO FOS | 24 hours +0.7% FOS | 24 hours NO FOS |
|---|---|---|---|---|
| GR4 | 7.38 | 7.41 | 0 | 7.55 |
| L1525 | 7.57 | 7.7 | 0 | 8.26 |
| L1544 | 7.48 | 7.42 | 0 | 7.6 |
| L1508 | 7.19 | 7.13 | 0 | 7.03 |
| L1512 | 7.3 | 7.33 | 0 | 8.12 |
| L336 | 7.52 | 7.36 | 0 | 7.89 |
| Mean | 7.41 | 7.39 | 0 | 7.74 |
| STD | 0.14 | 0.18 | 0 | 0.45 |

At the end of the incubation period the pH of the solutions in each flask was measured and was found to be approximately 7.25 when FOS was omitted from the system. When FOS was included in the model, the pH was found to be approximately 5.5.

Conclusions

Inclusion of FOS in a model of the canine large intestine resulted in the elimination of viable *Campylobacter jejuni* cells. With no FOS added to the system, *Campylobacter jejuni* cells were able to survive for the duration of the experiment with no fall in numbers. It is likely that the difference in pH observed between the two conditions was responsible for the difference observed in survival. It is likely that the non-pathogenic, saccharolytic bacteria present in the faeces metabolise the FOS and produce SCFA that decrease the pH in the model of the large intestine used in this study and this decrease in pH cannot be tolerated by Campylobacter.

EXAMPLE 2

The Effect of Galactooligosaccharide (GOS) on the Survival of *Campylobacter jejuni* in a Model of the Canine Intestine Method The method used was as per Example 1 substituting FOS for GOS. The results from the individual experiments are shown in Table 2. GOS was from Borculo Domo ingredients (BDI).

Results

After a 24-hour microaerobic incubation, no viable *Campylobacter jejuni* cells could be recovered from flasks that had GOS added. In contrast, *Campylobacter jejuni* cells were recovered from the flasks that contained no GOS at around 10$^8$ cells per ml. The results from the 6 individual experiments are shown in Table 2.

TABLE 2

Numbers of viable *Campylobacter jejuni* cells (log$_{10}$) recovered from the model of the canine large intestine with and without the addition of GOS.
←----log$_{10}$ colony forming units of *Campylobacter jejuni* ---→

| Faecal Sample | 0 hours +0.7% GOS | 0 hours NO GOS | 24 hours +0.7% GOS | 24 hours NO GOS |
|---|---|---|---|---|
| GR1 | 7.28 | 7.23 | 0 | 8.71 |
| L1550 | 7.42 | 7.2 | 0 | 8.68 |
| L136 | 7.15 | 7.09 | 0 | 8.88 |
| L1526 | 7.06 | 7.13 | 0 | 7.22 |
| L1515 | 7.58 | 7.59 | 0 | 8 |
| GR3 | 7.11 | 7.18 | 0 | 7.3 |
| Mean | 7.27 | 7.24 | 0 | 8.13 |
| STD | 0.2 | 0.18 | 0 | 0.74 |

At the end of the incubation period the pH of the solutions in each flask was measured and was found to be approximately 7 when GOS was omitted from the system (SD of 0.1). When GOS was included in the model, the pH was found to be approximately 5 (SD of 0.26).

Conclusions

Inclusion of GOS in a model of the canine large intestine resulted in the elimination of viable *Campylobacter jejuni* cells. With no GOS added to the system, *Campylobacter jejuni* cells were able to survive for the duration of the experiment. It is likely that the difference in pH observed between the two conditions was responsible for the difference observed in survival. It is likely that the non-pathogenic, saccharolytic bacteria present in the faeces metabolise the GOS and produce SCFA that decrease the pH in the model of the large intestine used in this study and this decrease in pH cannot be tolerated by Campylobacter.

EXAMPLE 3

The Effect of Coconut Endosperm Fibre on the Survival of *Campylobacter jejuni* in a Model of the Canine Intestine Method Investigation into the effect of coconut endosperm fibre on the survival of Campylobacter in the canine intestine.

Summary

Campylobacter is one of the most predominant gastrointestinal pathogens causing both clinical and non-clinical infections in dogs.

An in vitro model of the canine large intestine has been developed to test the effect of novel fibres on the survival of canine bacterial pathogens.

Inclusion of coconut endosperm fibre in this model resulted in the elimination of viable *Campylobacter jejuni* cells from the system.

Methods

*Campylobacter jejuni* cells were grown from stock cultures and cultured at 37° C. under microaerobic conditions (5% $O_2$, 10% $CO_2$ and 85% $N_2$). Liquid cultures were grown in 20 ml volumes in 50 ml conical flasks shaken on an orbital shaker. Overnight cultures grown in Mueller Hinton (MH) broth (Oxoid) were adjusted to $A_{600}$ 1.0 before inclusion in the assay.

Flasks were set up with 200 ml MH broth, 1 ml of the adjusted *Campylobacter jejuni* culture, and 2 g fresh faeces. To test flasks, 0.7% (w/v) copra cake was added and swirled to mix. Control flasks had no further additions.

Flasks were sampled at the start (0 hours) and end (24 hours) of the experiment to determine viable counts of *Campylobacter jejuni* cells by serially diluting samples from the flasks and plating dilutions on to Campylobacter selective agar (LabM). Plates were incubated microaerobically for 48 hours, after which viable numbers were determined.

At the end of the experiment the pH of the mixture in each flask was determined using Multistix (Bayer).

The experiment was conducted six times using a faecal sample from a different dog each time. All dogs were fed a commercially available premium (complete and balanced) dry food for the duration of the study.

Results

After a 24 hour microaerobic incubation, no viable *Campylobacter jejuni* cells could be recovered from flasks that had coconut endosperm fibre added. In contrast, *Campylobacter jejuni* cells were recovered from the flasks that contained no coconut endosperm fibre at around $10^8$ cells per ml. The results from the 6 individual experiments are shown in the table below and in the graph in FIG. 1.

TABLE 3

Numbers of viable *Campylobacter jejuni* cells ($log_{10}$) recovered from the model of the canine large intestine with and without the addition of coconut endosperm fibre.

⟵---------$log_{10}$ colony forming units of *Campylobacter jejuni*---------⟶

| Faecal Sample (Dog No) | 0 hours < +0.7% | 0 hours Coconut None | 24 hours Endosperm +0.7% | 24 hours Fibre> None |
|---|---|---|---|---|
| 1 | 7.76 | 7.75 | 0 | 7.25 |
| 2 | 7.33 | 7.64 | 0 | 8.56 |
| 3 | 7.77 | 7.75 | 0 | 7.17 |
| 4 | 7.72 | 7.74 | 0 | 7.47 |
| 5 | 7.67 | 7.71 | 0 | 8.59 |
| 6 | 7.16 | 7.38 | 0 | 8.97 |
| Mean | 7.57 | 7.66 | 0 | 8 |
| STD | 0.26 | 0.14 | 0 | 0.79 |

FIG. 1 shows a graph of the effect of the inclusion of coconut endosperm fibre in the canine large intestine model on the survival of *Campylobacter jejuni*. Letters denote statistically significant difference (p<0.05).

Recorded pH after 24 hours incubation with coconut endosperm fibre included and omitted from the system for each dog.

| Dog No. | +0.7% Coconut endosperm fibre | No Coconut endosperm fibre |
|---|---|---|
| 1 | 6.75 | 7.5 |
| 2 | 6.25 | 7.5 |
| 3 | 6.75 | 7.5 |
| 4 | 6.25 | 7.5 |
| 5 | 6.25 | 7.5 |
| 6 | 6.25 | 7.5 |

At the end of the incubation period the pH of the solutions in each flask was measured and was found to be 7.5 when coconut endosperm fibre was omitted from the system (SD of 0). When coconut endosperm fibre was included in the model, the pH was found to be 6.42 (SD of 0.26).

Conclusion

Inclusion of coconut endosperm fibre in a model of the canine large intestine resulted in the elimination of viable *Campylobacter jejuni* cells. With no coconut endosperm fibre added to the system, *Campylobacter jejuni* cells showed no loss in viability for the duration of the experiment. As a pH range of 6.5 to 7.5 is optimum for Campylobacter, it is unlikely that the difference in pH observed between the two conditions was responsible for the difference observed in survival. Instead, it is likely that the non-pathogenic, saccharolytic bacteria present in the faeces metabolise the coconut endosperm fibre. *Campylobacter jejuni* is incapable of fermenting carbohydrates, thus the coconut endosperm fibre being present gives the non-pathogenic, saccharolytic bacteria an advantage.

EXAMPLE 4

The Effect of Galactooligosaccharide (GOS) on the Survival of *Salmonella enterica* Serotype Typhimurium in a Model of the Canine Large Intestine Salmonella is one of the most predominant gastrointestinal pathogens causing both clinical and non-clinical infections in dogs.

Shedding of Salmonella in faeces can continue for 3 to 6 weeks increasing zoonotic risk in humans especially young children.

An in vitro model of the canine large intestine has been developed to test the effect of non-digestible carbohydrates on the survival of canine bacterial pathogens.

Inclusion of GOS in this model resulted in the elimination of viable *S. enterica* serotype Typhimurium cells from the system. This translates to a reduction in shedding times of Salmonella in a host animal.

Studies were undertaken to determine whether the inclusion of the prebiotic galactooligosaccharide (GOS) in an in vitro model of the canine large intestine would have any effect on the survival of a key pathogen of interest in dogs, Salmonella. GOS was obtained from Borculo Domo Ingredients and the product name is lactifit.

Method

*S. enterica* serotype Typhimurium (strain 7128) cells were grown from stock cultures and cultured at 37° C. Liquid cultures were grown in 20 ml volumes in 50 ml conical flasks shaken on an orbital shaker. Overnight cultures grown in Mueller Hinton (MH) broth (Oxoid) were adjusted to $A_{600}$ 1.0 before inclusion in the assay.

Flasks were set up with 200 ml MH broth, 1 ml of the adjusted Salmonella culture, and 2 g fresh faeces. To test flasks, 1.4 g GOS (CG86) was added and swirled to mix. Equivalent of 0.7% w/v. Control flasks had not further additions.

Flasks were sampled at the start (0 hours) and end (24 hours) of the experiment to determine viable counts of Salmonella cells by serially diluting samples from the flasks and plating dilution's onto Salmonella selective agar (LabM). Plates were incubated for 48 hours after which, viable numbers were determined.

At the end of the experiment the pH of the mixture in each flask was determined using pH Boy (Camlab Limited, Nuffield Road, Cambridge, CB4 1TH).

The experiment was conducted six times using a faecal sample from a different dog each time. All dogs were fed a commercially available premium (complete and balanced) dry food.

Results

After a 24 hour microaerobic incubation, no viable Salmonella cells could be recovered from the flasks supplemented with GOS. In contrast, Salmonella cells were recovered from the flasks that contained no GOS at around $10^7$ cells per ml. The results from the 6 individual experiments are shown in the table below and in FIG. 2.

TABLE 4

Number of viable S. enterica serotype Typhimurium cells ($\log_{10}$) recovered from the model of the canine large intestine with and without the addition of GOS.
←---$\log_{10}$ colony forming units of S. enterica serotype Typhimurium---→

| Faecal Sample | 0 hours +0.7% GOS | 0 hours NO GOS | 24 hours +0.7% GOS | 24 hours NO GOS |
|---|---|---|---|---|
| GR1 | 6.53 | 6.4 | 0 | 7.78 |
| L1550 | 6.16 | 6.06 | 0 | 7.25 |
| L136 | 6.47 | 6.48 | 0 | 7.86 |
| L1502 | 6.25 | 6.09 | 0 | 7.32 |
| L1515 | 6.41 | 6.3 | 0 | 7.11 |
| GR3 | 6.51 | 6.25 | 0 | 7.77 |
| Mean | 6.39 | 6.26 | 0 | 7.52 |
| STD | 0.15 | 0.17 | 0 | 0.32 |

Figure 2:
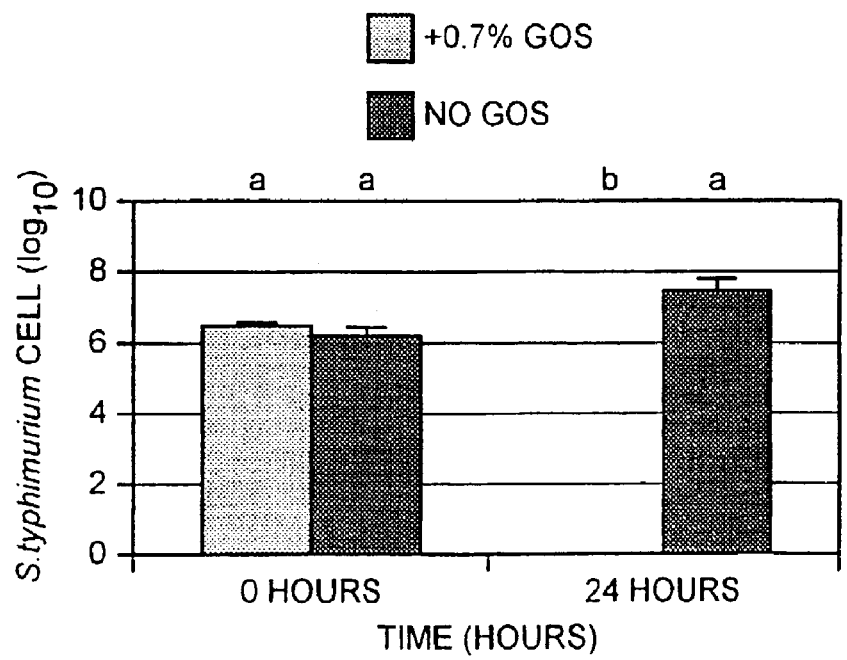
FIG. 2 is a graph in a graph of *S. typhimurium* cells at 0 and at 24 hours in incubation with or without GOS.

FIG. 2. Graph to show the effect of the inclusion of GOS in the canine large intestine model on the survival of S. enterica serotype Typhimurium. Different letters denote statistically significant difference ($p<0.05$).

At the end of the incubation period the pH of the solutions in each flask was measured and was found to be 7.2 when GOS was omitted from the system (SD of 0.26). When GOS was included in the model, the pH was found to be 5.1 (SD of 0.17).

Conclusion

Inclusion of GOS in a model of the canine large intestine resulted in the elimination of viable Salmonella cells. With no GOS added to the system, Salmonella cells were able to survive for the duration of the experiment. It is likely that the non-pathogenic, saccharolytic bacteria present in the faeces metabolise the GOS and produce SCFA that decrease the pH in the model of the large intestine used in this study and this decrease in pH cannot be tolerated by Salmonella. Thus it is likely that the difference in pH observed between the two conditions was responsible for the difference observed in survival. Salmonella is capable of fermenting carbohydrates but it is unlikely that it is capable of fermenting GOS, thus the presence of GOS gives the non-pathogenic, saccharolytic bacteria an advantage. Saccharoloytic bacteria increase in numbers and produce end products of fermentation that inhibit the growth of Salmonella.

Appendix 1

The Englyst method, from Englyst and Cummings (Supra).

Experimental Apparatus

The fractionation procedure was carried out in 50-60 ml screw-topped glass centrifuge tubes as previously described. Gas-liquid chromatography was performed with a Pye Unicam Series 204 chromatograph, fitted with a flame-ionisation detector. A 2.1 m×2 mm i.d. glass column packed with Supelcoport (100-200 mesh) coated with 3% SP 2330 was used. The column temperature was 215° C. (isothermal) and the injector and detector temperatures were 250° C. The carrier gas (nitrogen) flow-rate was 20 ml min$^{-1}$.

Reagents

High purity certified reagents were used for all analyses. Enzyme preparations were as follows: hog pancreatic α-amylase, E.C.3.2.1.1. (Sigma, Cat. No. A4268); pullulanase, E.C.3.2.1.41. (Boehringer, Cat. No. 108944).

Methods

The sequence of steps in the procedure is summarised below.

Pre-Treatment of Sample

As far as possible, foods should be analysed without any pre-treatment. If there are problems in taking a representative sample, foods with a low water content can be ball milled for 2-3 minutes, and those with a higher water content homogenised, or freeze-dried and ball milled.

Sample Mass

Accurately weigh between 50 and 1,000 mg of sample, containing not more than 150 mg of starch and 50 mg of NSP, into a 50-60 ml screw-top centrifuge tube and add a stirrer.

Fat Extraction and Drying

Samples with dry matter between 90 and 100% and with less than 203% of fat can be analysed directly. Otherwise, add 40 ml of acetone, mix for 30 minutes by using a magnetic stirrer, centrifuge and remove by aspiration as much of the supernatant as possible without disturbing the residue. Place the tubes in a water bath at 65° C. on a magnetic stirrer hot plate and mix the residue for a few minutes until it appears to be dry. The beaker can be covered and the acetone vapour removed by water pump.

Dispersion of the Starch

Add 2 ml of DMSO, cap the tube and heat it in a boiling water bath for 1 hour, timed from when re-boiling commences, stirring continuously. Then, without cooling, add 8 ml of 0.1M sodium acetate buffer pH5.2, at 50° C. and vortex mix immediately.

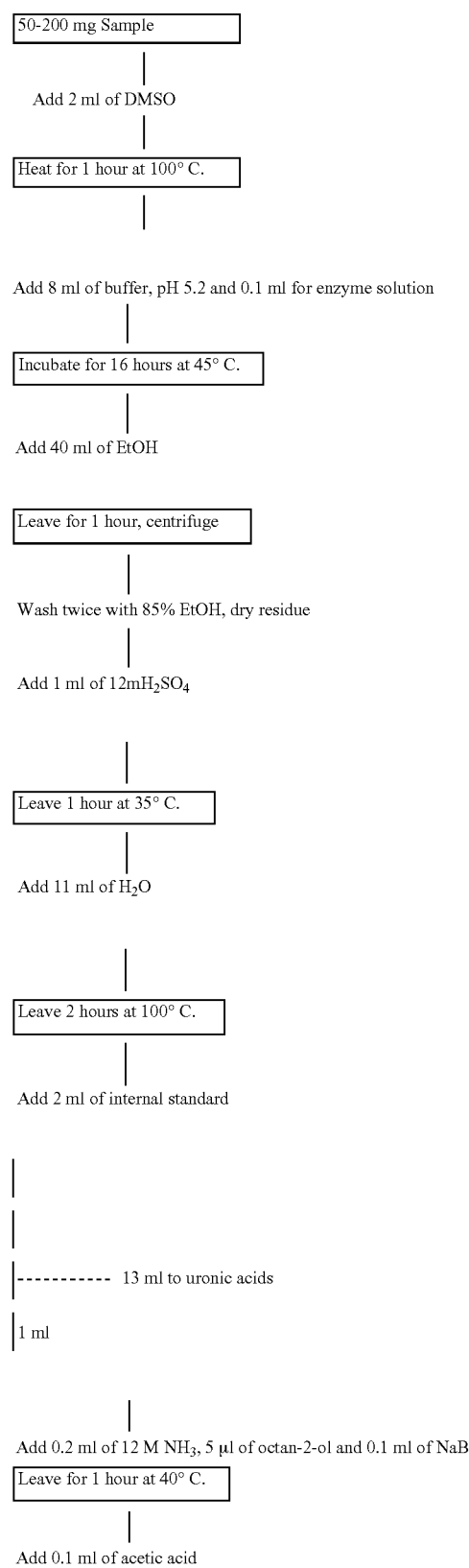

Procedure for the analysis of non-starch polysaccharides (NSP).

Enzyme Hydrolysis of the Starch

Cool the tube to 45° C. and immediately add 0.1 ml of an enzyme solution containing 5,000 units of α-amylase and 5 units of pullulanase per ml of acetate buffer at pH 5.2. Incubate the samples at 45° C. for 16-18 hours, preferably mixing continuously as described previously.

Following the enzyme treatment, add 40 ml of absolute ethanol, mix well and leave to stand for 1 hour at room temperature. Centrifuge for 10 minutes or until a clear supernatant liquid is obtained. Removed by aspiration as much of the supernatant liquid as possible, without disturbing the residue, and discard it. Wash the residue twice with 50 ml of 85% ethanol by mixing to form a suspension, centrifuging until clear and removing the supernatant liquid as before. Add 40 ml of acetone to the washed residue, stir for 5 minutes and then centrifuge. Remove the supernatant liquid by aspiration and dry the residue as described under Fat extraction and drying.

Acid Hydrolysis of the Residue from Enzymic Digestion

Disperse the dried residue in 1 ml of 12M sulphuric acid, using a vortex mixer. Leave at 35° C. for 1 hour to solubilise the cellulose, then rapidly add 11 ml of water and mix.

Heat the solution in a boiling water bath for 2 hours from re-boiling, stirring continuously. Cool it to room temperature by placing the tube in water, add 2 ml of internal standard (2 mg of allose per ml of saturated benzoic acid solution) and mix the contents of the tube. Use 1 ml of the hydrolysate for the preparation of alditol acetates and keep the remainder for the determination of uronic acids.

Uronic Acids

The method used is a modification of the method of Scott. Mix 0.3 ml of hydrolysate (diluted, if necessary, so that it contains between 25 and 100 μg of uronic acids per ml) with 0.3 ml of a mixtures of sodium chloride-boric acid solution (prepared by adding 2 g of sodium chloride and 3 g of boric acid to 100 ml of water) Add 5 ml of concentrated sulphuric acid and vortex mix, then place the tube in a heating block at 70° C. Leave the tube and contents for 40 minutes and then cool them to room temperature by placing in water. When cool, add 0.2 ml of 3.5-dimethylphenol solution (0.1 g of $(CH_3)_2$-$C_6H_3OH$ in 100 ml of glacial acetic acid) and mix immediately. Between 10 and 15 minutes later read the absorbance at 400 and 450 nm in a spectrophotometer against a water reference. Subtract the reading at 400 nm from that at 450 nm for each sample and plot the difference obtained for glucuronic acid standards (over the range 25-125 μf ml$^{-1}$). Read the sample concentrations from the graph.

Preparation of Alditol Acetates

To 1 ml of hydrolysate add 0.2 ml of 12M ammonia solution and 5 µl of octan-2-ol. Test that the solution is alkaline, and then add 0.1 ml of a freshly prepared solution of 100 mg of sodium tetrahydroborate (III) (sodium borohydride) per ml of 3M ammonia solution. Mix, leave the mixture for 1 hour at 40° C. and add 0.1 ml of glacial acetic acid. Next, to 0.2 ml of the acidified solution add 0.3 ml of N-methylimidazole and 2 ml of acetic anhydride, and mix. Leave it for 10 minutes at 20° C. (room temperature), add 5 ml of water, mix, and when cooled add 1 ml of dichloromethane, agitate the contents vigorously on a vortex mixer and centrifuge for a few minutes to separate the mixture into two phases. Remove the bulk of the upper phase by aspiration and discard it, then transfer the lower phase to a small vial, seal and store it at −20° C. Use 1-2 µl for injection on to the chromatograph.

Alternative Preparative of Alditol Acetates

When dichloromethane is used as a solvent for the alditol acetates it has been observed in a number of laboratories without automatic GLC injection facilities that the injection technique is critical to the obtaining of reproducible results. A more robust method can be obtained if dichloromethane is replaced with ethyl acetate as a solvent for alditol acetates. The procedure is as follows:

To 1 ml of hydrolysate add 0.2 ml of 12M ammonia solution and 5 µl of octan-2-ol. Test that the solution is alkaline, then add 0.1 ml of a freshly prepared solution of 100 mg of sodium tetrahydroborate (III) per ml of 3M ammonia solution. Mix, leave the mixture for 1 hour at 40° C. and add 0.1 ml of glacial acetic acid. To 0.5 ml of the acidified solution add 0.5 ml of N-methylimidazole, 5 ml of acetic anhydride and mix. Leave for 10 minutes at 20° C. (room temperature), then add 0.6 ml of ethanol and mix. After 5 minutes add 5 ml of water, place in a water bath at room temperature, add 5 ml of 7.5M KOH and a few minutes later a further 5 ml of 7.5M KOH. Mix by inverting and leave to separate into two phases. Transfer the top phase to a small vial and store at +5° C. Use 1-2 µl for injection on the chromatograph.

It is to be understood that, while the invention has been described in conjunction with the detailed description thereof, the foregoing description is intended to illustrate and not limit the scope of the invention. Other aspects, advantages, and modifications of the invention are within the scope of the claims set forth below.

What is claimed is:

1. A method for treating a pathogenic Campylobacter, *Escherichia coli* or Salmonella bacteria in a large intestine of a dog or cat, the method comprising the step of administering to the dog or cat a pet food product comprising of a non-digestible carbohydrate which is,
    a) a dietary fiber source selected from the group consisting of coconut endosperm fiber, beet pulp, citrus pulp, rice bran, carob bean or gum talha and combinations thereof, and/or
    b) an oligosaccharide selected from the group consisting of galactooligosaccharide, maltooligosaccharide, xylooligosaccharide, raffinose and combinations thereof,
    wherein the pet food product is administered to deliver the non-digestible carbohydrate of a) and/or b), in an amount sufficient to treat the pathogenic Campylobacter, *Escherichia coli* or Salmonella bacteria in the large intestine of the dog or cat.

2. The method of claim 1, wherein the pathogenic bacteria is *Campylobacter jejuni* or *Salmonella enterica*.

3. The method of 1, wherein the pathogenic bacteria is *Campylobacter jejuni* and the non-digestible carbohydrate comprises a galactooligosaccharide.

4. The method of claim 1, wherein the pathogenic bacteria is *Salmonella enterica* Serotype Typhimurium and the non-digestible carbohydrate comprises a galactooligosaccharide.

5. The method of claim 3 or 4 wherein the pet food is administered in an amount sufficient to cause a decrease in intestinal pH thereby treating the pathogenic bacteria.

6. The method of claim 1, wherein the pathogenic bacteria is *Campylobacter jejuni* and the non-digestible carbohydrate comprises a coconut endosperm fiber.

* * * * *

UNITED STATES PATENT AND TRADEMARK OFFICE
CERTIFICATE OF CORRECTION

PATENT NO. : 7,608,291 B2  
APPLICATION NO. : 10/221423  
DATED : October 27, 2009  
INVENTOR(S) : Baillon et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 821 days.

Signed and Sealed this

Twelfth Day of October, 2010

David J. Kappos  
*Director of the United States Patent and Trademark Office*